United States Patent
Kapoor et al.

(10) Patent No.: US 11,771,396 B2
(45) Date of Patent: Oct. 3, 2023

(54) QUANTIFICATION OF BLOOD FLOW WITH ULTRASOUND B-MODE IMAGING

(71) Applicant: Siemens Medical Solutions USA, Inc., Malvern, PA (US)

(72) Inventors: Ankur Kapoor, Plainsboro, NJ (US); Tommaso Mansi, Plainsboro, NJ (US); Kutay F. Ustuner, Mountain View, CA (US); Helene C. Houle, San Jose, CA (US); Ismayil M. Guracar, Redwood City, CA (US); Rickard C. Loftman, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1297 days.

(21) Appl. No.: 15/909,570

(22) Filed: Mar. 1, 2018

(65) Prior Publication Data
US 2019/0269379 A1    Sep. 5, 2019

(51) Int. Cl.
*A61B 8/06* (2006.01)
*A61B 8/08* (2006.01)

(52) U.S. Cl.
CPC .............. *A61B 8/06* (2013.01); *A61B 8/5223* (2013.01); *A61B 8/5246* (2013.01); *A61B 8/481* (2013.01); *A61B 8/488* (2013.01)

(58) Field of Classification Search
CPC ..... A61B 8/5223; A61B 8/5246; A61B 8/481; A61B 8/488; A61B 8/06; A61B 8/065; A61B 8/48; A61B 8/483; A61B 8/52; A61B 8/5215; A61B 8/5238; A61B 8/5261; A61B 8/5269; A61B 8/5276; G06T 7/0012; G06T 7/20; G01F 1/66; G01F 1/663; G01F 1/666
See application file for complete search history.

(56) References Cited

U.S. PATENT DOCUMENTS

| | | | | |
|---|---|---|---|---|
| 5,685,308 | A * | 11/1997 | Wright | G01S 15/8988 600/443 |
| 5,855,557 | A * | 1/1999 | Lazenby | A61B 8/488 600/443 |
| 6,527,717 | B1 * | 3/2003 | Jackson | A61B 8/5276 600/443 |
| 8,241,216 | B2 | 8/2012 | Loftman et al. | |
| 8,690,781 | B2 | 4/2014 | Loftman et al. | |

(Continued)

OTHER PUBLICATIONS

Udesen et al.: High frame-rate blood vector velocity imaging using plane waves: simulations and preliminary experiments, IEEE Trans Ultrason Ferroelectr Freq Control. Aug. 2008, vol. 55 No. 8, (p. 1729-1743) (Year: 2008).*

(Continued)

*Primary Examiner* — Oommen Jacob (57) ABSTRACT

For quantification of blood flow by an ultrasound system, B-mode images generated with a multi-transmit, coherent image formation produce swirling or other speckle patterns in the blood regions. These patterns, as represented in specially formed B-mode images, are tracked over time to indicate two or three-dimensional velocity vectors of the blood at a B-mode resolution. Various visualizations may be provided at the same resolution, including the velocity flow field, flow direction, vorticity, vortex size, vortex shape, and/or divergence.

12 Claims, 3 Drawing Sheets
(1 of 3 Drawing Sheet(s) Filed in Color)

(56) References Cited

U.S. PATENT DOCUMENTS

| | | | |
|---|---|---|---|
| 8,992,429 B2* | 3/2015 | Sato | G01S 15/8981 600/453 |
| 9,142,061 B2* | 9/2015 | Metaxas | G06T 13/20 |
| 9,629,615 B1* | 4/2017 | Tavakoli | A61B 8/0883 |
| 9,972,069 B2* | 5/2018 | Tsadok | G06T 7/38 |
| 2005/0043622 A1* | 2/2005 | Jensen | G01S 15/8915 600/407 |
| 2005/0228279 A1 | 10/2005 | Ustuner et al. | |
| 2006/0173313 A1 | 8/2006 | Liu et al. | |
| 2008/0269611 A1* | 10/2008 | Pedrizzetti | A61B 8/06 600/454 |
| 2009/0326379 A1* | 12/2009 | Daigle | A61B 8/06 600/453 |
| 2010/0210943 A1* | 8/2010 | Mahmoud | A61B 8/4245 600/437 |
| 2011/0208056 A1* | 8/2011 | Datta | A61B 8/5223 600/441 |
| 2012/0283568 A1* | 11/2012 | Loftman | G10K 11/346 600/447 |
| 2014/0050048 A1* | 2/2014 | Jensen | G01S 15/8977 367/7 |
| 2015/0045644 A1* | 2/2015 | Comaniciu | A61B 5/02007 600/407 |
| 2015/0080725 A1* | 3/2015 | Wegner | G01S 15/8997 600/440 |
| 2015/0141832 A1* | 5/2015 | Yu | G01S 15/8984 600/455 |
| 2015/0164473 A1* | 6/2015 | Kim | A61B 8/4494 600/443 |
| 2015/0342567 A1 | 12/2015 | Ustuner et al. | |
| 2016/0140730 A1* | 5/2016 | Falahatpisheh | G01S 15/89 382/131 |
| 2016/0228190 A1* | 8/2016 | Georgescu | A61B 8/065 |
| 2019/0269379 A1* | 9/2019 | Kapoor | G16H 50/30 |

OTHER PUBLICATIONS

Gao et al.: Left ventricular 2D flow pattern estimation of the heart by combining speckle tracking with Navier-Stokes based regularization, IEEE International Ultrasonics Symposium Proceedings. Oct. 2010, (p. 1068-1071) (Year: 2010).*

Hansen et al.: Vector velocity estimation of blood flow—A new application in medical ultrasound, Ultrasound, Nov. 2017, vol. 25 No. 4, (p. 189-199) (Year: 2017).*

Song ["Speckle Tracking in 3D Echocardiography with Motion Coherence", 2007 IEEE Conference on Computer Vision and Pattern Recognition]. (Year: 2007).*

Zotkin ["Plane-Wave Decomposition of Acoustical Scenes Via Spherical and Cylindrical Microphone Arrays" IEEE Transactions on Audio, Speech, and Language Processing, vol. 18, No. 1, Jan. 2010]. (Year: 2010).*

U.S. Appl. No. 15/364,132, filed Nov. 29, 2016.

Rickard Loftman, Ph.D. "IN Focus Coherent Technology" White Paper (2007): 1-8.

* cited by examiner

QUANTIFICATION OF BLOOD FLOW WITH ULTRASOUND B-MODE IMAGING

BACKGROUND

The present embodiments relate to blood flow imaging with ultrasound. Either Doppler ultrasound or ultrasound imaging of injected contrast agents are used to determine the blood velocity in a patient. In the case of Doppler, the ultrasound only measures the velocity perpendicular to the insonification direction. To compute streamlines or vorticity, two or three-dimensional velocity vectors in the scan plane or volume of ultrasound are needed. In methods that use Doppler, the velocity vectors are computed indirectly by assuming conservation of mass inside the volume or region of interest. This assumption is valid only under certain heart phases when the net flow in the chambers is small. Doppler ultrasound may also have a lesser spatial resolution than anatomy imaging using B-mode.

In the case of contrast agent imaging, microbubbles injected into the patient are tracked. The half-life of ultrasound contrast agents is short. Since microbubbles are not retro-reflective, the contrast agent imaging is highly sensitive to the insonification direction. Both these factors make contrast agent imaging for monitoring flow overly sensitive to user variability and image acquisition.

SUMMARY

By way of introduction, the preferred embodiments described below include a method, instructions and systems for quantification of blood flow by an ultrasound system. B-mode images generated with a multi-transmit, coherent image formation produce swirling or other speckle patterns in the blood regions. These patterns, as represented in specially formed B-mode images, are tracked over time to indicate two or three-dimensional velocity vectors of the blood at a B-mode resolution. Various visualizations may be provided at the same resolution, including the velocity flow field, flow direction, vorticity, vortex size, vortex shape, and/or divergence.

In a first aspect, a method is provided for quantification of blood flow by an ultrasound system. The ultrasound system scans a heart of a patient, and B-mode images are generated with synthetic transmit aperture. The B-mode images include speckle for response from blood. A flow field of two or three-dimensional velocities of the blood is determined from the speckle response for the blood of the B-mode images. A flow image that as a function of the velocities of the flow field is displayed.

In a second aspect, a method is provided for quantification of blood flow by an ultrasound system. The ultrasound system scans blood of a patient. B-mode images are formed with multi-transmit, coherent image formation. Two or three-dimensional velocity vectors of the blood are determined from the B-mode images. A flow image that is a function of the velocity vectors is displayed.

In a third aspect, an ultrasound system is provided for quantification of blood flow. A transmit beamformer is configured to generate waveforms for transmit events. A B-mode detector is configured to generate a sequence of B-mode images. Each of the B-mode images is responsive to multiple of the transmit events for each of a plurality of locations. An image processor is configured to determine blood flow parameters from pattern tracking the sequence of B-mode images. A display configured to generate a flow image of the blood flow parameters.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Intraventricular blood flow is quantified using B-mode images where each B-mode image is formed using multiple transmissions to a same location and coherent image processing. In ultrasonic imaging of heart chambers, coherent image formation techniques based on multiple transmit events produce swirling patterns in the chambers. These patterns are interpreted to uncover quantitative and/or qualitative information about blood flow dynamics.

Blood flow velocity and/or acceleration are computed using multi-pulse non-collinear coherent imaging techniques. The spatially varying response to motion is accounted for in the calculations, allowing determination of various vortex parameters to indicate pathological conditions in the heart, especially in 3D.

By using the information from coherent imaging, it is possible to reconstruct velocity and acceleration fields with high frame rate and sensitivity. Interpretation of these patterns is not straightforward as there is a spatially varying response to blood flow velocity due to varying synthesis counts in the imaging field. This spatially varying response may be handled by including a prior model in the tracking and/or by limiting variation in velocity in the tracking. A prior model derived from a simulation of fluid dynamics using information of the heart structure extracted from any B-mode image may be used to improve the pattern tracking. Responsive measurements may be augmented with boundary conditions derived from heart structure and fluid dynamics simulations to derive more accurate flow information.

Accurate heart disease diagnosis is provided by measuring the velocity vectors, streamline distribution, and/or vorticity distribution of blood flow inside the heart without the need for ultrasound contrast agents. Velocity and other flow parameters of intracardiac and intravascular blood velocities flow field are determined without the need for contrast agents. Assumptions about direction of the velocity may be avoided.

Figure 1:
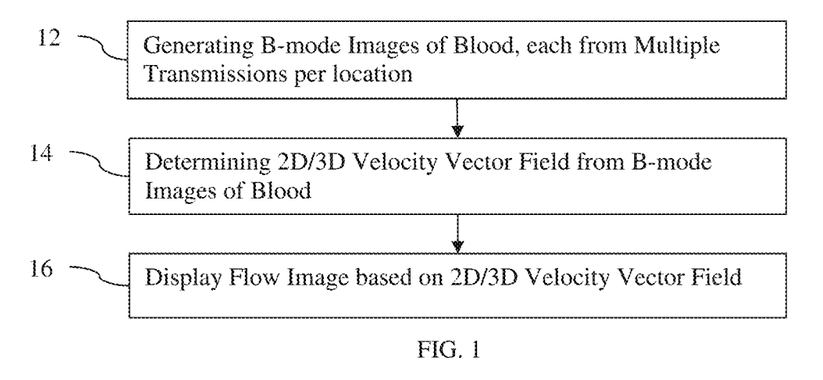
FIG. 1 is a flow chart diagram of one embodiment of a method for quantification of blood flow by an ultrasound system.

FIG. 1 shows one embodiment of a method for quantification of blood flow by an ultrasound system. Patterns created when ultrasound beams interact with blood or any fluid medium are tracked over time, providing velocities as two or three-dimensional vectors. As compared to typical or regular B-mode imaging, B-mode imaging using multi-pulse coherent combination provides patterns responsive to the blood that may be more easily tracked. Intra-cardiac or intra-vascular blood flow parameters are provided using B-mode data rather than contrast agents or Doppler imaging.

Figure 2:
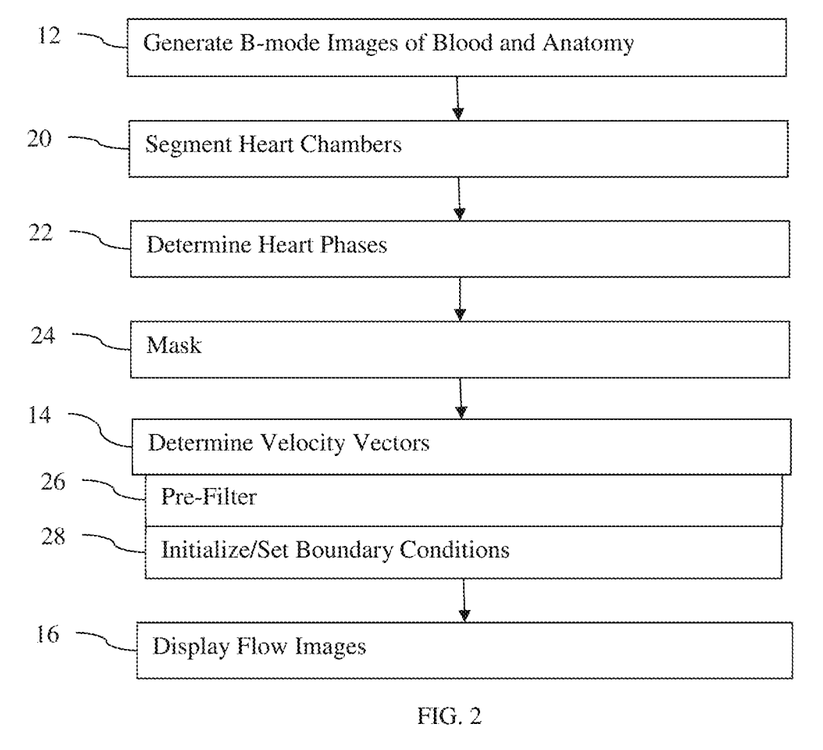
FIG. 2 is a flow chart diagram of another embodiment of a method for quantification of blood flow by an ultrasound system.

FIG. 2 shows another embodiment of a method for quantification of blood flow by an ultrasound system. This embodiment includes additional acts. The method is a further example for imaging blood flow in a heart of a patient using ultrasound-based, multi-pulse, coherent B-mode imaging. FIGS. 1 and 2 are discussed together below.

Figure 4:
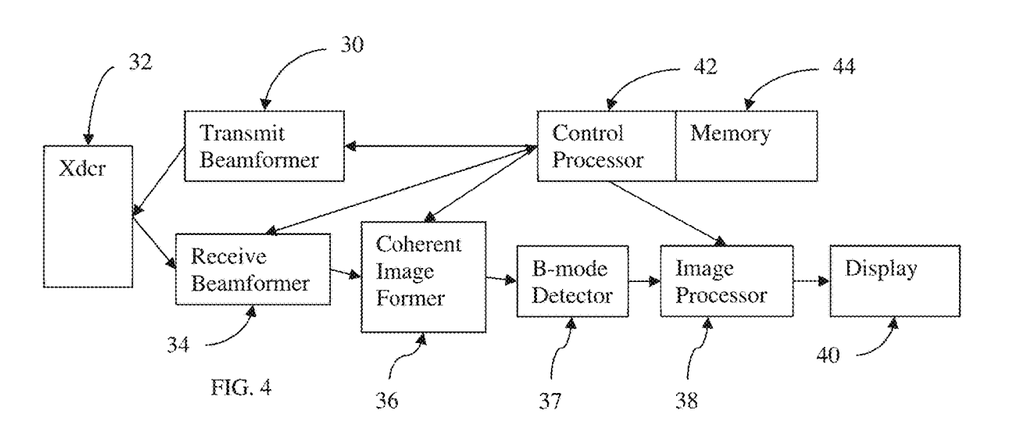
FIG. 4 is a block diagram of one embodiment of a system for quantification of blood flow.

The methods of FIGS. 1 and 2 are performed by the system of FIG. 4 or a different system. For example, beamformers, a coherent image former (e.g., coherent data combination), and a B-mode detector perform act 12. An image processor performs acts 14 and 20-28. An image processor creates the images displayed on a display device in act 16. Other devices, such as a workstation, server, or computer may perform the non-scanning acts.

Additional, different or fewer acts may be provided. For example, various acts 20-28 of FIG. 2 are not performed. As another example, acts for configuring the ultrasound system or implementing the particular type of image formation are provided.

The acts are performed in the order shown (i.e., numerically or top to bottom). The acts may be performed in other orders, such as performing act 26 prior to acts 20, 22, and/or 24.

In act 12, the ultrasound system generates B-mode images with multi-pulse, coherent image formation. In typical B-mode imaging, each sample location (e.g., pixel or beamformer sample location in the scan pattern) is scanned once to create the image. The log compressed intensity of the echo from the location is calculated from one receive sample per location. Each receive sample is acquired using a fixed transmit focus and dynamic focus on receive.

For multi-pulse coherent image formation, multiple transmit events and corresponding receive events are used for each location. The data from the multiple receive events for each location is combined. For a given multi-pulse coherent B-mode image, each pixel or sample location represented by the B-mode image is from a combination of data responsive to multiple transmit beams covering that pixel or location. Coherent image formation techniques in ultrasound imaging that utilize multiple transmit events per output pixel may create a time varying signature in the B-Mode image of blood. With multi-pulse, coherent image formation for B-mode, blood flow creates a time varying signature similar to flow of smoke particles. The data resulting from the multi-pulse, coherent combination may be detected using B-mode detection to produce are pattern for response from fluid.

The combination relies on the coherence of the data. The data being combined includes phase information. For receive beamformed ultrasound data, the relative phase and magnitude are maintained, such as using in-phase (I) and quadrature (Q) data or radio frequency (RF) data output by the receive beamformer. For channel data (i.e., data from transducer elements prior to beamformation across the aperture), the RF signal includes phase information.

The combination may occur prior to beamformation, such as using adaptive beamforming of channel data. In other embodiments, the combination occurs after beamformation. For example, the post-beamformation coherent imaging taught in U.S. Published Application No. 2018/0149734 (Ser. No. 15/364,132, filed Nov. 29, 2016) is used. The coherence between beamformed samples is used in the combination. In one embodiment, the coherent image formation taught in U.S. Pat. No. 8,690,781 or 8,241,216 is used. Other transmit aperture synthesis may be used.

In one embodiment of coherent image formation of B-mode images, harmonic imaging using combination of data is used. Contrast agents may be imaged with harmonic imaging where the signals at frequencies other than the transmitted fundamental frequency are processed. Example harmonics include fractional and integer harmonics, such as the second or cubic fundamental. Rather than just applying a filter, multiple transmissions may be performed with different relative phasing (e.g., opposite polarity) and/or magnitude. The responsive data from these transmissions is combined, cancelling out the signal at the fundamental due to phasing and leaving the signal at the harmonic. The coherence of the transmit waveforms is used.

In another embodiment, the coherent image formation uses synthetic transmit aperture. For scanning, the ultrasound system uses a fixed transmit focus or no focus (e.g., transmit a single beam, a wide beam, a diverging wave front, or a beam with infinite focus). Synthetic transmit aperture uses multiple transmissions, the geometry of the scanning, and responsive data with coherent information to synthesize the transmit focus for the aperture. Any synthetic transmit aperture or focusing may be used.

In one embodiment, parallel receive beamforming forms receive beams in response to a transmit event over an area or volume insonified by the transmit event. This is repeated for other transmit events insonifying the area or volume. Dynamic focus provides receive focusing specific to each location. The transmit focus is fixed, or the transmit wave front has an infinite or no focus. Examining the data retrospectively for each depth in the image, the many beams per transmit provide many unique transmit interrogations of each point in the image. When the data of these multiple transmit events are adjusted in time, phase, and amplitude for each single depth in the image, data from each transmit event provides information to synthesize transmit focus. This information is echo data relevant to a subset of the active transmit aperture. This subset is in a region where a point of tangency may be achieved between the actual and desired transmit wave front. By applying a stationary phase approximation to the Huygens-Fresnel integral model for pressure in the body, the transmit aperture is synthesized. Since phasing is used, the resulting data is formed by coherent combination.

In another embodiment, the synthetic transmit aperture image formation taught in U.S. Published Application No. 2015/0342567 is used. Post-beamforming synthetic aperture ultrasound imaging adapts to coherence metrics of data used to synthesize. Adaptive discrimination techniques are applied based on post-beamformation signals used in retrospective transmit focus synthesis. Signals generated from acoustic clutter or incoherent noise sources or fast-moving targets have lower temporal coherence and/or higher phase dispersion. By calculating the correlation coefficients and/or phase shifts for every point among collinear receive beams or functions of these variables, weighting functions are computed and applied either to individual collinear beam components before summation or to the output image after coherent summation, or both. During aperture synthesis of transmit focus, an output beam is produced by coherently summing ultrasound data (e.g., beamformed data) from a number (e.g., 5) of collinear receive beams after geometry-based delay and phase adjustment and scaling of individual component beams. The ultrasound data is combined using both the relative phase and amplitude, analytically synthesizing ultrasound data representing the collinear beams.

In contrast to array beamforming, the adaptation operates on post-beamforming data, data that has had a first focusing operation performed already. The phase, delay, and/or scaling may be based on a coherence metric, such as correlation coefficients or phase changes, or functions of these parameters based on colinear receive beams or data from the same locations.

B-mode detection is applied to the multi-pulse, coherently combined beamformed data. The log compressed intensity from B-mode detection of the input data form the combination provides a multi-pulse, coherently formed B-mode image.

The transmit focus or aperture may be synthesized from channel data in other embodiments. The channel data received in response to multiple transmissions is combined to synthesize a transmit focus for each location. The geometry alone or geometry and a coherence metric are used to synthesize the transmit focus. The resulting data is beamformed and applied to a B-mode detector.

The B-mode image is a frame of data after B-mode detection. The frame of data may be scalar values without phase information. The B-mode image is an image in the sense that the B-mode image represents the patient over space. The B-mode image may be from the data path after B-mode detection, from before or after scan converting to a display format, from before or after greyscale mapping to display values of the display device, and/or from before or after actual display on the display device.

The B-mode image represents a multi-dimensional region of the patient, such as having two or three spatial dimensions. A sequence of such images is obtained, such as a sequence of B-mode images over one, more, or a part of a heart cycle. Each of the B-mode images is based on B-mode detection for a frame of data formed from multi-pulse, coherent image formation.

The ultrasound system generates the multi-pulse, coherently formed B-mode images by scanning blood of a patient. For example, the heart of the patient is scanned. By using multi-pulse, coherent image formation and then B-mode detecting, the multi-pulse, coherently formed B-mode images include speckle or other pattern for response from the blood. Rather than relying on tissue movement or tracking of speckle from tissue, the blood response may be used despite use of B-mode imaging. Blood flow may be tracked without contrast agents. The apparent motion of the pattern formed due to interaction of multi-pulse, coherent image formation in B-mode ultrasound with the blood in the heart chambers or vasculature is trackable to determine velocities.

In act 20, the flow region is segmented. For example, one or more heart chambers are segmented. The locations of the tissue boundaries of the flow region are determined. The boundaries over time are located.

The segmentation uses the multi-pulse, coherently formed B-mode images. Alternatively, the scanning interleaves multi-pulse, coherent formation of B-mode images with regular B-mode imaging (e.g., B-mode images formed with a fixed transmit focus or single pulse). The segmentation uses the regularly formed B-mode images. Alternatively, the scanning for multi-pulse, coherent image formation is provided, but regular B-mode images as well as multi-pulse, coherently formed B-mode images are generated from the same data. The segmentation uses the regularly formed B-mode images.

Any segmentation may be used. Image processing, such as using random walker, thresholding, gradient, and/or pattern matching, may locate the tissue boundary. A heart or tissue model may be fit to the data to locate the tissue boundary. In other embodiments, a machine-learnt classifier or network is used. The B-mode image or information derived therefrom is input as feature vector values to the network. The network outputs locations of the tissue boundary based on machine-learnt knowledge from training images and known or expert annotated ground truth.

In act 22, the heart phases for the images are determined. The scanning may be triggered. An ECG signal is used to scan the patient at particular phases and/or throughout a given phase. In other embodiments, the scanning occurs regularly or constantly. Analysis of the scan data or B-mode images may be used to derive the phase, or ECG signals are used to assign phases to the images.

Images associate with the periods of specific phases may be identified. For example, end diastole, end systole, and/or a phase for constant volume (ICV) are used. The phase used may depend on the cardiac decease or imaging application. Images in a given cycle and/or over multiple cycles for the selected phase or phases are used for further processing. Alternatively, images over the entire heart cycle are used.

In act 24, the multi-pulse, coherently formed B-mode images are masked. The segmentation is used to mask. The mask removes or prevents use of data from tissue. The flow region or regions of interest are isolated by the masking. The pattern caused by multi-pulse, coherent combination for the B-mode image is isolated for tracking.

In act 14, an image processor determines two or three-dimensional velocity vectors of the blood from the multi-pulse, coherently formed B-mode images. Rather than finding the velocity just towards or away from the transducer, the direction and magnitude of velocity in two or three dimensions is determined.

Velocity vectors are determined for each sample location or pixel represented by the multi-pulse, coherently formed B-mode images. A flow field of vectors for the fluid region is determined. This flow field has a same resolution as the multi-pulse, coherently formed B-mode images. The velocities of the blood have a same resolution or spatial density as the B-mode image or scan sampling.

The image processor determines the velocity vector at each location using pattern tracking. A pattern in a neighborhood (e.g., 10×10 pixels) around the location in one image is located in another image by correlation (e.g., minimum sum of absolute differences or cross-correlation). Different spatial displacements are tested, and the spatial displacement with a greatest correlation is identified. This spatial displacement provides the distance and direction. The time between the scanning and/or generation of the images provides the time. The velocity vector is determined for each location by the respective distance, direction, and time. By repeating tracking through a sequence, the velocity vectors over time are determined.

Other approaches for pattern tracking may be used. With reference to FIG. 2, partial differential equations are used to determine the velocities by tracking the time varying signatures (e.g., patterns) over time.

In act 26, a filter or image processor implementing a filter spatially filters the multi-pulse, coherently formed B-mode images. Linear or nonlinear filtering may be used. The coherent image formation may result in a greater number, density, or resolution along one dimension as compared to another. To interpolate to make the image more or completely isotropic, anisotropic filtering may be applied. The pattern from the masked blood flow region is filtered. Alternatively, temporal filtering or no filtering is applied.

In one embodiment, the anisotropic pre-filter is a Gaussian kernel. The kernel may be square or other shape where the weights of the kernel have an anisotropic distribution.

In another embodiment, a Wronskian filter replaces each element or B-mode intensity at location (i,j) in the output by the Wronskian of a (w+1)×(w+1) matrix centered around (i,j). "w" may be any size for defining the neighborhood, such as w=4.

Another alternative is a graph-based filter. Each element or B-mode intensity at location (i,j) is replaced with the Fielder's number based on the algebraic connectivity of a graph G with (w+1)×(w+1) edges centered about (i,j). The edges of the graph are the connectivity between adjacent pixels or locations (i,j) in the input image, and the nodes are the pixels or element.

To solve the partial differential equations, an iterative optimization is used. The function being optimized includes one or more energy terms.

In act 28, the boundary conditions are set, and the optimization is initialized. For example, boundary conditions limiting the deviation or variance of the velocity direction and/or magnitude as a function of space are established. For example, the acceleration, curl, and/or divergence of the velocity vectors from neighbors may be limited. As another example, a default velocity distribution for the application (e.g., heart) is used. In one embodiment, a model specific to the patient is used to calculate the initial flow field based on fluid dynamics.

Equation 1 shows one example of the function being solved.

$$[u(t),v(t)]=\min_{(u,v)\in\Omega\times[0,T]} E_{data}+\alpha E_{smooth}+\beta E_{prior} \quad (1)$$

where t is time, u is velocity in one direction, v is velocity in a periductular direction to u, C) is the spatial distribution of the masked flow region, α and β are regularizing weights, $E_{data}$ is a pattern tracking term, $E_{smooth}$ is a term limiting velocity variance, and $E_{prior}$ is a model term. Additional, different, or fewer energy terms may be used. A different function for tracking may be used.

u and v are aligned to the fluid region. For example, u and v are the long and short axes of a heart chamber. In other embodiments, u and v are aligned with the scanning, such as u being depth and v being lateral.

α and β sum to 1 for relatively weighting the energy terms initializing and/or limiting the flow field solution. α and β may be constant. α and β may vary as a function of location. For example, the multi-pulse, coherently formed B-mode image may have less fluid pattern available for tracking at the tissue boundaries, so the velocities from the modeling are relied on more in the solution. Thus, β weights $E_{prior}$ more heavily at locations by the tissue boundary than elsewhere.

$E_{data}$ is a pattern tracking term. The multi-pulse, coherently formed B-mode images I are the data used for tracking. The images may be from the output of the pre-filtering of act 26. One example pattern tracking term is given by:

$$E_{data}=\int_{\Omega\times[0,T]}(\psi(|\nabla|^2)+|\nabla^2 I|^2)dx'dt \quad (2)$$

where $\psi(s^2)$ is an increasing concave function. For example, $\psi(s^2)=\sqrt{s^2+\in^2}$, for a small positive constant $\in$ and $\nabla$ is a difference operator. The choice of typically does not introduce additional parameters. Since $\in$ is added only for numerical reasons, it can be set to a fixed value, e.g. 0.0001. The difference in space (e.g., u and v directions) and in time, t, is used. Any difference operator may be provided for tracking, such as a gradient operator. In one embodiment, the gradient operator is given in 2D+t space by:

$$\nabla_3:=\partial_{xx}+\partial_{yy}+\partial_t \text{ and } \nabla_3 f=(f_x,f_y,f_t)^T \quad (3, 4)$$

where f is the velocity vector, x and y are directions, and t is time. x and y may be the directions for u and v, or other directions. The subscript "3" represents the 2D+t. 3D+t may be used.

$E_{prior}$ is a prior model of flow. The model provides a flow field over time or based on cardiac phase. The model may be generalized to the fluid region, such as a model of standard heart. The measured flow fields based on other patients may be used. In one embodiment, the model is specific to the patient. The segmentation of act 20 is used to fit a model to the anatomy of the patient. Computational fluid dynamics is then used with the fit model and a pressure to calculate the velocity vectors at the different locations. The pressure in the heart may be assumed or measured, such as extrapolating the heart chamber pressure from a cuff measured pressure. This simulation of fluid dynamics in the heart structure for the heart of the patient (e.g., chamber walls, and/or valve dimensions and locations) provides estimated velocity vectors.

$E_{smooth}$ is a boundary condition term. Any boundary conditions for the velocity vectors and/or parameters used to derive the velocity vectors may be used. In one embodiment, $E_{smooth}$ is modeled as:

$$E_{smooth}=\int_{\Omega\times[0,T]}(\psi(|\nabla u|^2+|\nabla v|^2)dxdt \quad (5)$$

$E_{smooth}$ is an illustrative example of the smoothing of acceleration or change in velocity. In other embodiments, the curl, divergence, or other characteristic of the velocity vectors (e.g., magnitude and direction) are limited to regularize the final vector field. The limitation is over space and/or time.

Since the smoothing term includes the velocity components for which equation 1 solves, an iterative optimization to fit the velocity vectors to the data and prior is used. Any optimization may be used, such as L2 norm, L1, or total variation (TV). In alternative embodiments, the flow field is determined without iterative optimization.

The output is a field of 2D or 3D velocity vectors in 2D or 3D space for each or one time. The pattern of response from blood in B-mode images is used to derive the flow field at a resolution of the multi-pulse, coherently formed B-mode images without having to inject contrast agents.

In act 16, the image processor generates a flow image, which is displayed on a display device. The ultrasound system maps values for the ultrasound data to display values (e.g., RGB). The display values are loaded into a display plane, from which the display generates the image.

For the flow image, the velocity vectors are mapped to display values. For locations with a threshold magnitude of velocity, the magnitude of velocity or other single characteristic of flow may be the scalar mapped to the image. Greyscale or color mapping may be used. In other embodiments, the flow information is mapped to color, allowing at least two characteristics to be mapped for flow locations. For example, the magnitude is mapped to color and direction is mapped to brightness. In yet other embodiments, graphics are generated. The flow information is used to position, size, color, and/or other characteristic of one or more graphics (e.g., lines, arrows, contours, and/or alphanumeric annotation).

The flow information is provided for each pixel, voxel, or sample location of the fluid region. The image may include flow information at a same resolution or spatial density as B-mode information. For locations in the image without flow, the B-mode information may be mapped to greyscale. The multi-pulse, coherently combined B-mode image or a standard (e.g., single transmit) B-mode image is used. The flow information is overlaid or combined with the B-mode image, providing a flow image that is a combination with the B-mode image.

Figure 3A:
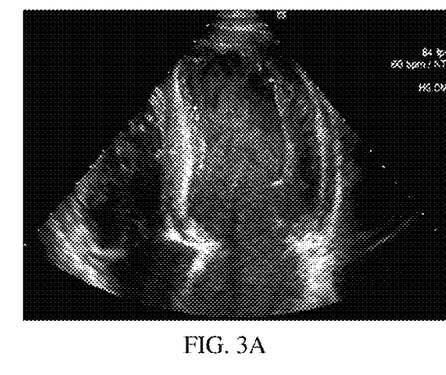
FIG. 3A shows an example B-mode image formed with transmit aperture synthesis.

FIG. 3A shows a multi-pulse, coherently formed B-mode image. Tissue is shown around the edges or sides of the image. In the center is a heart chamber. The pattern detected from blood is visible rather than being dark as occurs in typical B-mode imaging.

The flow image is a function of the velocities of the flow field. The velocity vectors are used to generate the flow image. The velocity vectors or characteristic of the velocity vectors are mapped to the display values as the flow image. Alternatively, the flow information is derived from the velocity vectors. A sequence of flow images may allow the viewer to visualize the changes in flow.

In one embodiment, a vector field is generated as the flow image. The velocity vectors, averaged by neighborhood, are mapped to arrow graphics. Any number and/or size of arrow graphics may be used. The magnitude of the vector maps to arrow length, color, and/or width. The direction of the vector maps to direction of the arrow.

Figure 3B:
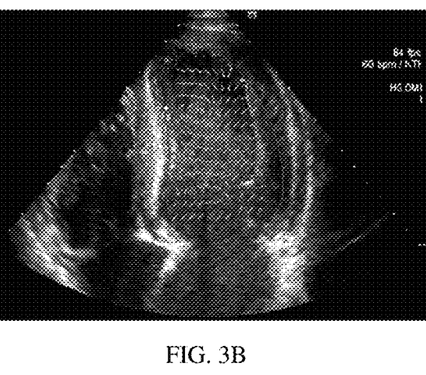
FIGS. 3B-F show different flow images generated by tracking the pattern of response from blood.

FIG. 3B shows the same B-mode image of FIG. 3A with the flow information mapped as a vector field. The segmented tissue border is highlighted in red. The arrows represent the flow paths or directions, as well as the magnitude of flow mapped to length of the arrows. Within this tissue border, the arrows are derived from the velocity vectors. The direction and magnitude of the flow at the time represented by the image during the heart phase are shown.

Figure 3C:
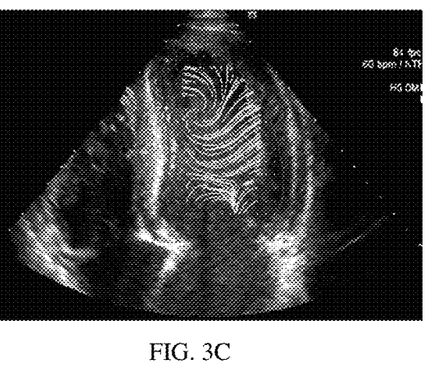

FIG. 3C shows another embodiment where flow lines or streamlines are derived from the velocity vectors. The flow direction is found by fitting lines, mapping contours, or thresholding. The directions from the velocity vectors are used to find flow paths in the fluid region. Lines or curves are graphically added to indicate the flow paths. The color, width, or brightness of the lines may be based on the average magnitude of flow along the flow path. Alternatively, the flow line graphics show the direction information without magnitude information.

In other embodiments, the flow information being at a same resolution as the B-mode image allows for other visualizations of flow derived from the pattern in B-mode response. For example, the vorticity is derived from the flow field of velocity vectors. The amount of rotation or curl (e.g., rate change in one direction with respect to an orthogonal direction) is determined for each location. A neighborhood, such as immediately adjacent locations, is used to calculate the vorticity at each location of flow. This curl measure of the flow field is mapped to the display image, such as mapping to color.

Figure 3D:
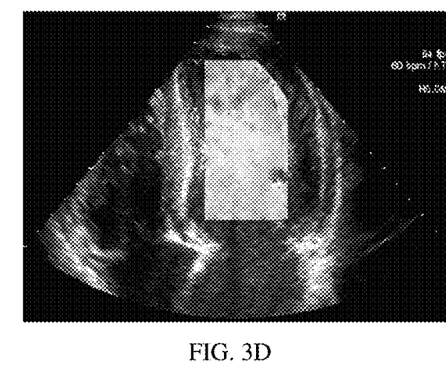

FIG. 3D shows an example where vorticity is mapped to color at a same resolution as the B-mode image. The pseudo-colored image represents the curl or vorticity of the computed flow field overlaid on the multi-pulse, coherently formed B-mode ultrasound image. For a two-dimensional field, vorticity may be considered a scalar quantity and is color mapped with intensity proportional to strength or rate and color proportional to direction (in/out of plane or clockwise/counterclockwise).

In the application of intercardiac flow, the location of the primary vortex is considered as an indicator of disease. Thus, the presented visualization allows a quick determination of the center of the vortex without the need to focus on arrows or streamlines that may be noisy. The vorticity image assists in identification of the location of vortices and the location and strength of the primary vortex with respect to the anatomy (e.g. wall, valves, etc.). In the example of FIG. 3D, the strongest vorticities are shown in red and blue (clockwise and counter clockwise).

Additionally or alternatively, the vorticity in the flow field is used to derive further flow information. The size and/or shape of one or more vortices are determined from the calculated vorticity. A threshold is applied to identify regions of higher vorticity. The threshold is a default value or adapts to the levels of vorticity for a given patient or image. Alternatively, local peaks of vorticity are identified, and region growing is applied.

Low pass filtering, clustering, or other image processing may be applied to the results of the thresholding. Based on size, peak vorticity, shape, and/or other characteristic of the resulting regions, one or more of the regions are selected. The boundary of each region is identified. A graphic showing the boundaries is used as the flow image. The boundary line may be colored, sized, or have brightness based on the peak or average vorticity of the corresponding vortex.

Figure 3E:
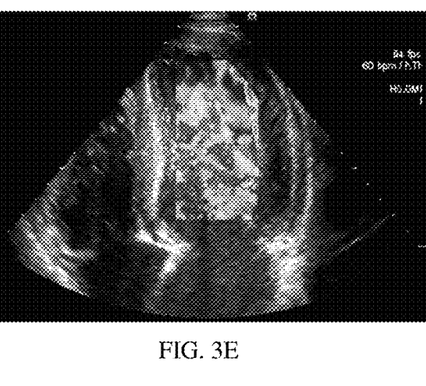
Figure 3F:
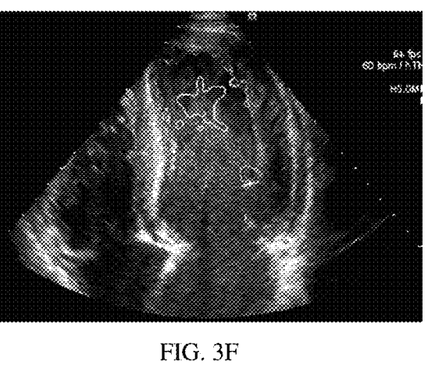

FIG. 3F shows an example of displaying the flow image with sizes and shapes of vortices indicated in the flow image. Six vortices are shown by adding vortex boundary lines at the boundaries, providing both size and shape. These vortices are determined based on the vorticity shown in FIG. 3D. Contours are overlaid on the B-model ultrasound image to assist in determination of the extents of the vortices with respect to the anatomy (e.g. wall, valves, etc.). Calculated size may be provided as an alphanumeric annotation. The size represents the extent of the vortex, and the center is represented by the contour location. Determining the location of the vortices in the intercardiac flow assists diagnosis. The plots of the vortices help visual localization of the vortices.

In another example benefiting from the flow information being at a same resolution as the B-mode image, the flow image shows the divergence derived from the flow field. The divergence is derived from the velocity vectors or vorticity. The degree or rate at which flow in adjacent locations is directed away from each given location is determined. In one embodiment, the inner product of the operator del and a vector is calculated, giving a measure of the quantity of flux emanating from any point of the vector field. The divergence is mapped to color or graphics.

FIG. 3E shows the divergence of the flow field mapped to color as the flow image. The pseudo-colored image representing the divergence of the computed flow field is overlaid on the B-model ultrasound image to assist in identification of the directionality (counterclockwise/clockwise) of the vortices with respect to the anatomy (e.g. wall, valves, etc.). The absolute value of the divergence of the field is mapped to the color. The divergence shows the flow fields "source." In the context of intercardiac flow, where it is important to determine the directionality (counterclockwise/clockwise) of the vortex, the time series visualization of divergence of the field may highlight this quantity. In this case, the user can appreciate the direction of flow based on the intensity of the mapped pseudo-color. The motion of most intense pseudo color (blue/red) is the indicated direction of the flow.

FIG. 4 shows one embodiment of a system for quantification of blood flow. The system implements the method of FIG. 1, the method of FIG. 2, or another method. Synthetic transmit aperture or other multi-transmit with coherence is used to generate data, which is then B-mode detected. The resulting B-mode image includes a pattern from response of fluid. The patterns are tracked through a sequence of such B-mode images deriving flow information.

The system is a medical diagnostic ultrasound imaging system. The system includes a transducer 32, a transmit beamformer 30, a receive beamformer 34, a coherent image former 36, detector 37, an image processor 38, a display 40, a control processor 42, and a memory 44. Additional, different or fewer components may be provided, such as including a scan converter and/or user interface.

The transducer 32 is an array of a plurality of elements. The elements are piezoelectric or capacitive membrane elements. The array is configured as a one-dimensional array, a two-dimensional array, a multidimensional array, combinations thereof, or any other now known or later developed array. The transducer elements transduce between acoustic and electric energies. The transducer 32 connects with the transmit beamformer 30 and the receive beamformer 34 through a transmit/receive switch, but separate connections may be used in other embodiments.

The transmit beamformer 30 is a processor, delay, filter, waveform generator, memory, phase rotator, digital-to-analog converter, amplifier, combinations thereof, or any other now known or later developed transmit beamformer components. The transmit beamformer 30 may have a plurality of channels for generating electrical signals of a transmit waveform for each element of a transmit aperture on the transducer 32. The waveforms may have relative delay or phasing and amplitude for focusing the acoustic energy. The transmit beamformer 30 is configured by loading a sequence by a controller. To transmit a transmit beam or wave front, the controller sets an aperture (e.g. the number of active elements), an apodization profile across the plurality of channels, a delay profile across the plurality of channels, a phase profile across the plurality of channels and/or combinations thereof. Any acoustic wave front for transmit aperture synthesis may be used, such as a focused beam, a broad beam with infinite focus or focus outside the field of view, or a diverging wave front.

The receive beamformer 34 is a preamplifier, filter, phase rotator, delay, summer, base band filter, processor, buffers, memory, combinations thereof or other now known or later developed receive beamformer components. The receive beamformer 34 has a plurality of channels for receiving electrical signals representing echoes or acoustic energy impinging on the transducer 32. Beamforming parameters including a receive aperture (e.g., the number of elements and which elements are used for receive processing), the apodization profile, a delay profile, a phase profile and combinations thereof are applied to the receive signals for receive beamforming. For example, relative delays and amplitudes or apodization dynamically focus the acoustic energy along one or more scan lines. The relatively delayed or phased channel data is summed to beamform. A control processor controls the various beamforming parameters for receive beam formation. Multiple receive beams may be formed in response to each transmit event.

The control processor 42 is a general processor, digital signal processor, field programmable gate array, application specific integrated circuit, digital circuit, analog circuit, or combinations thereof. The control processor 24 is configured by software, firmware, and/or hardware to control the image forming process and/or to calculate flow information. As part of the image forming process, the control processor 42 sets a scan pattern or acquisition sequence.

The beamformer parameters used by the transmit beamformer 30, the receive beamformer 34, or both are set for transmit aperture synthesis. Transmit wave fronts focused at a region or diverging through the flow region (e.g., small aperture or single element) insonify the same locations multiple times. The responsive echoes are received by the transducer 32 and converted into electrical signals for each element (i.e., channel data). Receive beamformation with dynamic focus may be applied to the channel data. Either the channel data or the receive beamformed data responsive to the different transmissions is used to retrospectively synthetize a transmit aperture. The synthesis alters or combines the data using coherence to emulate data as if the transmit had been focused at the location. By synthesizing a transmit aperture for each location, data that is in-focus or two-way focused for both transmit and receive is created.

The coherent image former 36 is a general processor, digital signal processor, control processor, application specific integrated circuit, digital circuit, digital signal processor, analog circuit, combinations thereof, or other now known or later developed processors for performing transmit aperture synthesis. In one embodiment, the coherent image former 36 is part of the receive beamformer 34, control processor 36, or image processor 38, but a separate or dedicated processor or circuit may be used in other embodiments. The coherent image former 36 includes memory buffers, complex multipliers and complex summers, but other components may be used. The coherent image former 36 is configured by software, firmware, and/or hardware. For example, the control processor 42 controls operation of the coherent image former 36 using codes or instructions buffered in the image former 36.

The coherent image former 36 is configured to synthesize a transmit aperture from channel data or receive beamform data. The coherence between data from different transmissions is used with the geometry of the scanning to synthesize the transmit apertures for transmit focus to each location despite the actual transmit event not being focused on the location. For example, the coherent image former 36 is operable to form data representing a range of depths or lateral locations or combine received data from different transmissions to form data with a synthesized transmit aperture. The coherent combination is prior to detection.

In one embodiment, using parallel receive beamformation, sets of data representing locations in at least a common field of view are obtained, each set in response to a transmit with a spatially distinct phase front. The common field of view receive data are time aligned and amplitude weighted for retrospective transmit focusing and retrospective transmit apodization, respectively. A time offset is applied to the receive data for retrospective transmit focusing. The offset is selected to emulate shifting the transmit delay profile to be tangentially intersecting with the dynamic receive delay profile for each location which is the desired transmit delay profile. A weight is applied to the receive data for retrospective transmit apodization. The offset and weighted data representing a same location from different transmit events is coherently combined. The number of sets of data offset, weighted and combined may vary as a function of depth for dynamic transmit beamformation.

The detector 38 is a general processor, digital signal processor, control processor, application specific integrated circuit, digital circuit, digital signal processor, analog circuit, field programmable gate array, combinations thereof, or other now known or later developed processors for envelope detection. The detector 38 is a B-mode detector. The detector 38 detects the amplitude, intensity (i.e., amplitude squared) or log-compressed amplitude or intensity. The detector 38 may include a scan converter. The scan converter reformats the ultrasound data from a scan format (e.g., polar coordinate) to a display format (e.g., Cartesian coordinate). Spatial and/or temporal filters may be included.

The detector 38 receives sequences of frames of data. The frames of data are formed by transmit aperture synthesis. The detection is applied to each of the frames of data, which are each frame is responsive to multiple transmit events to determine the value or data for each location. Due to the response from blood, the resulting multi-pulse, coherently formed B-mode images with patterns for fluid are output.

The image processor 38 is a same or different type of device as the control processor 42 and/or detector 37. The image processor 38 may be part of the control processor 42, the coherent image former 36, and/or the detector 37 or may be separate. The image processor 38 is configured to determine blood flow parameters from the sequence of B-mode images formed with synthetic transmit apertures. After any object detection (e.g., segmentation), masking, selection of desired cardiac phases and corresponding data, and/or filtering, the image processor 38 is configured to track the pattern from fluid response over time or between frames of data (e.g., B-mode images). Correlation or other tracking is performed to determine the velocity vectors based on the patterns. In one embodiment, an optimization solves differential equations to determine the velocity vectors. The B-mode images formed with synthetic transmit apertures with any boundary conditions and/or initialization are used for solving for the velocity vectors.

The image processor 38 generates a flow image. Flow information alone or combined with B-mode information is used in the image. B-mode information is mapped to greyscale values. Flow information is mapped to color and/or graphics. Flow information for one time, such as at a particular cardiac phase, is used for imaging. Flow information over times, such as represented in a sequence of images, may be used for imaging.

The flow information is blood flow parameters, such as the velocity vectors or information derived from the velocity vectors. Curl, flow direction, divergence, vortex size, vortex shape, and/or other blood flow parameters are derived and mapped to display values.

The display 40 is a monitor, LCD, LED, plasma, projector, printer, or other now known or later developed visual representation device. The display 40 includes a display plane into which display values for the flow image are loaded. The display 40 is configured by the stored display values to generate an image. The image is generated from the output of the image processor 38. One or more flow images are displayed. Any combination of images with or without annotation, graphics, or other information are displayed.

The instructions for implementing the adaptive processes, methods and/or techniques discussed above are provided on computer-readable storage media or memories 44, such as a cache, buffer, RAM, removable media, hard drive or other computer readable storage media. The instructions are implemented on a single device, such as the control processor 42, the beamformer 30, 34, the coherent image former 36, the detector 37, the image processor 38, and/or a plurality of devices in a distributed manner. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for quantification of blood flow by an ultrasound system, the method comprising:
generating, by the ultrasound system scanning a heart of a patient, B-mode images with synthetic aperture, the B-mode images including patterns in chambers of the heart for response from blood due to the synthetic aperture;
determining a flow field of two or three-dimensional velocities of the blood from the pattern response for the blood of the B-mode images, wherein determining comprises iteratively optimizing as a function of first and second energy terms, the first energy term comprising pattern tracking and the second energy term comprising a prior model of flow based on fluid dynamics in heart structure for the heart of the patient, the two or three-dimensional velocities determined at a resolution of the B-mode images; and
displaying a flow image as a function of the velocities of the flow field, the flow image having the resolution of the B-mode images for flow information, wherein displaying comprises: (a) displaying curl of the flow field mapped to color as the flow image, the curl having the resolution, or (b) displaying divergence of the flow field mapped to color as the flow image, the divergence having the resolution.

2. The method of claim 1 wherein generating the B-mode images with synthetic aperture comprises combining data from multiple transmit events for each location represented by each of the B-mode images.

3. The method of claim 1 wherein displaying the flow image further comprises displaying flow paths or flow direction derived from the flow field.

4. The method of claim 1 wherein displaying the flow image further comprises displaying a vector field of the velocities of the flow field.

5. The method of claim 1 wherein displaying the flow image further comprises displaying a vortex or vortex size and shape derived from the flow field.

6. The method of claim 1 wherein iteratively optimizing comprises iteratively optimizing as a function of the first energy term, the second energy term, and a third energy term, the third energy term comprising a smoothing term.

7. The method of claim 6 wherein iteratively optimizing the function comprises optimizing with the function including regularizing weights that vary as a function of location.

8. The method of claim 1 wherein determining comprises spatially filtering the each of the B-mode images with a linear or nonlinear filter.

9. The method of claim 8 wherein the filter comprises a Wronskian filter or a graph-based filter.

10. The method of claim 1 wherein displaying comprises displaying the curl of the flow field mapped to color as the flow image.

11. The method of claim 1 wherein displaying comprises displaying the divergence of the flow field mapped to color as the flow image.

12. The method of claim 1 wherein displaying comprises displaying the flow image with sizes and shapes of vortices indicated in the flow image.

* * * * *